(12) United States Patent
Choi

(10) Patent No.: US 6,327,893 B1
(45) Date of Patent: Dec. 11, 2001

(54) FILTER LAYER COMPARATIVE TESTING METHOD AND APPARATUS

(75) Inventor: Kyung-Ju Choi, Louisville, KY (US)

(73) Assignee: AAF McQuay, Louisville, KY (US)

( * ) Notice: Subject to any disclaimer, the term of this patent is extended or adjusted under 35 U.S.C. 154(b) by 0 days.

(21) Appl. No.: 09/454,852

(22) Filed: Dec. 7, 1999

(51) Int. Cl.⁷ .............................. G01N 15/08; G01M 3/04; B01D 29/00
(52) U.S. Cl. ................................ 73/38; 73/40.7; 210/489
(58) Field of Search ...................... 73/38, 40.7; 210/489; 250/435; 95/286; 376/277; 96/135

(56) References Cited

U.S. PATENT DOCUMENTS

| | | | |
|---|---|---|---|
| 3,276,597 | * 10/1966 | Mesek et al. | 210/489 |
| 3,614,421 | * 10/1971 | Alter et al. | 250/435 |
| 3,810,697 | 5/1974 | Steinberg | 356/103 |
| 4,055,075 | * 10/1977 | Allan et al. | 73/40.7 |
| 4,157,968 | * 6/1979 | Kronsbein | 210/489 |
| 4,213,768 | 7/1980 | Bauman et al. | 55/97 |
| 4,279,508 | 7/1981 | Everroad | 356/257 |
| 4,324,568 | * 4/1982 | Wilcox et al. | 95/286 |
| 4,384,474 | * 5/1983 | Kowalski | 73/38 |
| 4,387,993 | 6/1983 | Adrian | 356/336 |
| 4,446,099 | * 5/1984 | Schwind et al. | 376/277 |
| 4,494,403 | 1/1985 | Bowers et al. | 73/40.7 |
| 4,515,007 | * 5/1985 | Herman | 73/38 |
| 4,610,705 | * 9/1986 | Sarnosky et al. | 96/135 |
| 4,619,136 | * 10/1986 | Ortiz | 73/38 |
| 4,646,558 | * 3/1987 | Gualtieri et al. | 73/40.7 |
| 4,686,848 | * 8/1987 | Casselberry et al. | 73/38 |
| 4,772,390 | * 9/1988 | Kawai et al. | 210/651 |
| 5,203,201 | 4/1993 | Gogins | 73/38 |
| 5,244,480 | 9/1993 | Henry | 55/213 |
| 5,351,523 | * 10/1994 | Blackford et al. | 73/38 |
| 5,488,811 | 2/1996 | Wang et al. | 53/52 |
| 5,968,373 | 10/1999 | Choi | 210/806 |

FOREIGN PATENT DOCUMENTS

| | | | | |
|---|---|---|---|---|
| 000150266A2 | * 9/1985 | (EP) | | G01M/3/20 |
| 2252785A | * 7/1975 | (FR) | | B01D/35/00 |
| 63311145A | 12/1987 | (JP) | | G01N/65/08 |

OTHER PUBLICATIONS

Sindetec, Process and Device for Determining the Distribution by Size of Particles in Suspension in a Liquid, translation, May, 2001.*

* cited by examiner

Primary Examiner—Hezron Williams
Assistant Examiner—Jay L. Politzer
(74) Attorney, Agent, or Firm—Polster, Lieder, Woodruff & Lucchesi

(57) ABSTRACT

A filter media testing arrangement and method including a flow-through test tower composed of a preselected number of clamped modular rings capable of supporting test samples in adjacent or spaced position therein so as to comparatively measure and control pressure drop and particulate separation characteristics of test sample media.

23 Claims, 4 Drawing Sheets

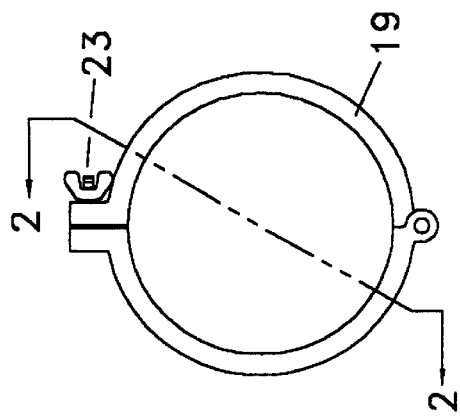
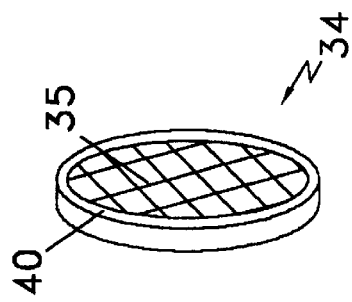
FIG 3
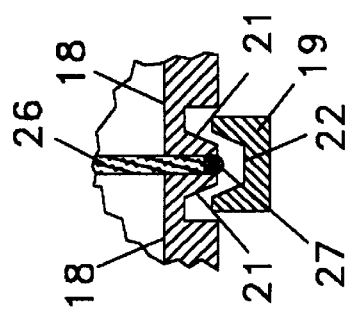
FIG 5
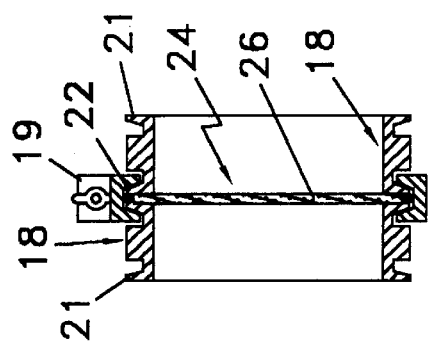
FIG 2
FIG 4

FILTER LAYER COMPARATIVE TESTING METHOD AND APPARATUS

BACKGROUND OF THE INVENTION

The present invention relates to filter testing equipment and more particularly to a method and apparatus for comparative testing of at least two successively aligned layers of filter media in a particulate laden fluid stream.

Testing devices for testing the integrity and/or efficiency of filter media are generally well known in the filtration art, attention being directed to such U.S. Pat. No. 3,810,697, issued to S. B. Steinberg on May 14, 1974; U.S. Pat. No. 4,213,768, issued to A. J. Bauman et al. on Jul. 22, 1980; U.S. Pat. No. 4,279,508, issued to H. L. Everroad on Jul. 21, 1981; U.S. Pat. No. 4,387,993, issued to R. J. Adrian on Jun. 14, 1983; U.S. Pat. No. 4,494,403, issued to C. W. Bowers et al. on Jan. 22, 1985 and, Japanese patent publication No. 6,331,114 5A of T. Kazuo on Dec. 19, 1988—all of which teach various efficiency and/or integrity testing embodiments for testing filter media. In addition, attention is further directed to U.S. Pat. No. 5,203,201, issued to M. A. Gogins on Apr. 20, 1993; U.S. Pat. No. 5,244,480, issued to H. G. Henry on Sep. 14, 1993; and, U.S. Pat. No. 5,488,811, issued to J. Wang et al. on Feb. 6, 1996—these three patents teaching filter testing arrangements which include structure for testing filter media in more than one position in a filtration system. Finally, attention is directed to MKS Instruments, Inc., Bulletin (cover pg. and ppgs. 14, 20 and 73). However, none of these aforementioned patents and bulletin even recognizes, let alone teaches, the importance of a comparative testing sample of at least two aligned filter media samples to be preselectively relatively positioned and/or spaced in aligned relation in the same filter testing system including a multi-stationed filter media sample holder. The inventive, unique and novel comparative filter media testing arrangement as disclosed herein, which allows for the control of differential pressure flow through filter media to be tested selectively maintaining the pressure drop across tested media substantially equal by varying media characteristics and spacing between tested media and/or the composition nature of tested media has particular applicability to U.S. Pat. No. 5,968,373, issued to Kyung-Ju Choi on Oct. 19, 1999. In order that appropriate filter media of preselected filtering properties and preselected layer spacing be incorporated in applicant's novel method and apparatus as set forth in the aforementioned U.S. Pat. No. 5,968,373, it is essential that each layer of filter media selected, as well as the relative spacing between layers, be carefully and accurately criteria compliant prior to further manufacture, assembly and subsequent replacement thereof. The novel filter media sample testing equipment as described herein permits the manufacture, assembly and replacement of layers of filter media and the replacement thereof in a straightforward and economical apparatus and method with a minimum of structural parts and with a minimum of operating steps—utilizing readily and variable assembled parts which are commercially and economically available for unrelated uses such as conduit piping. Various other features of the present invention will become obvious to one skilled in the art upon reading the disclosure set forth herein.

BRIEF SUMMARY OF THE INVENTION

More particularly the present invention provides a method of comparative testing at least two successive layers of filter media samples each of preselectively differing and successively controlled average pore size and/or fiber size, the selected filter media to be successively arranged in upstream-downstream respective alignment in a flow-through channel for removing particulate matter from a fluid stream to be treated in said channel comprising: successively positioning preselected sample layers of filter media which layers are to correspond to those to be utilized for filtering purposes with controlled average pore size and/or controlled fiber size arrangement respectively in a wall or fluid flow-through confined testing zone including an upstream inlet and a downstream outlet; the corresponding sample layers of filter media being supportively disposed in the confined flow-through testing zone between the upstream and the downstream outlet in preselected relation to each other to extend transversely across the line of fluid flow through the confined testing zone with the edges of the supported filter media sample layers being in sealed relation with the walls of the flow-through testing zone; introducing a measured particle laden fluid stream into the upstream inlet of the confined testing zone; and, measuring the particle count in the fluid upstream and downstream of each sample filter media layer. In addition, the novel method of the present invention provides for the inclusion of a controlled spacing step between layers to establish and/or meet any preselected spacing criteria. Further, the present invention provides for a unique and novel comparative test stand apparatus for comparatively testing successive layers of filter media samples to be utilized to optimize filtering capacity comprising: a flow-through housing having a fluid test stream inlet to receive preselected and measured particle laden fluids to be tested and a fluid test stream outlet downstream of the inlet; filter media sample receptacles cooperatively mounted with respect to the flow-through housing between the inlet and outlet to successively receive and relatively position at least two sample layers of filter media to be comparatively tested so that the sample layers are aligned with the fluid streams to be tested with the edges thereof in sealed relation with the inner wall faces of the flow-through housing; and; particle counter means associated with the housing to count particles in the fluid upstream and downstream of each filter media sample layer disposed in the housing. Further, the present invention includes a unique structural arrangement utilizing parts commercially available for other purposes and which provides for the adjusting and stacking and novel spacing in accordance with preselected spacing criteria between sample media layers to test whether the sample media layers are to be in face-to-face abutment or to be distanced from each other a preselected spaced distance.

It is to be understood that various changes can be made by one skilled in the art in one or more of the several parts and the several steps disclosed herein without departing from the scope or spirit of the present invention.

BRIEF DESCRIPTION OF THE DRAWINGS

FIG. 2 is an enlarged cross-sectional view of two aligned fluid flow-through conduits clamped together and which can be employed with the structure of FIG. 1 taken in a plane through line 2—2 of FIG. 3, the flow-through conduits being in the form of commercially available flow-through rings with extended peripheral flanges clamped together by a split, hinged clamping ring;

FIG. 3 is an enlarged plan view of the hinged clamping ring of FIG. 2;

FIG. 4 is an enlarged view of a portion of the filter sample arrangement as shown in FIGS. 2;

FIG. 5 is an enlarged isometric view of a support screen one or more of which can be adjustably positioned in a flow-through conduit to support and adjust spacing between two or more filter media in the novel testing tower of FIG. 1;

It is to be understood from the above examples of FIGS. 7–13, that other combinations of filter media test samples can be employed in the present invention, including more than two test samples and various media formations and various spaced relationships, all in accordance with the structure and method of the present invention.

DETAILED DESCRIPTION OF THE INVENTION

Figure 1:
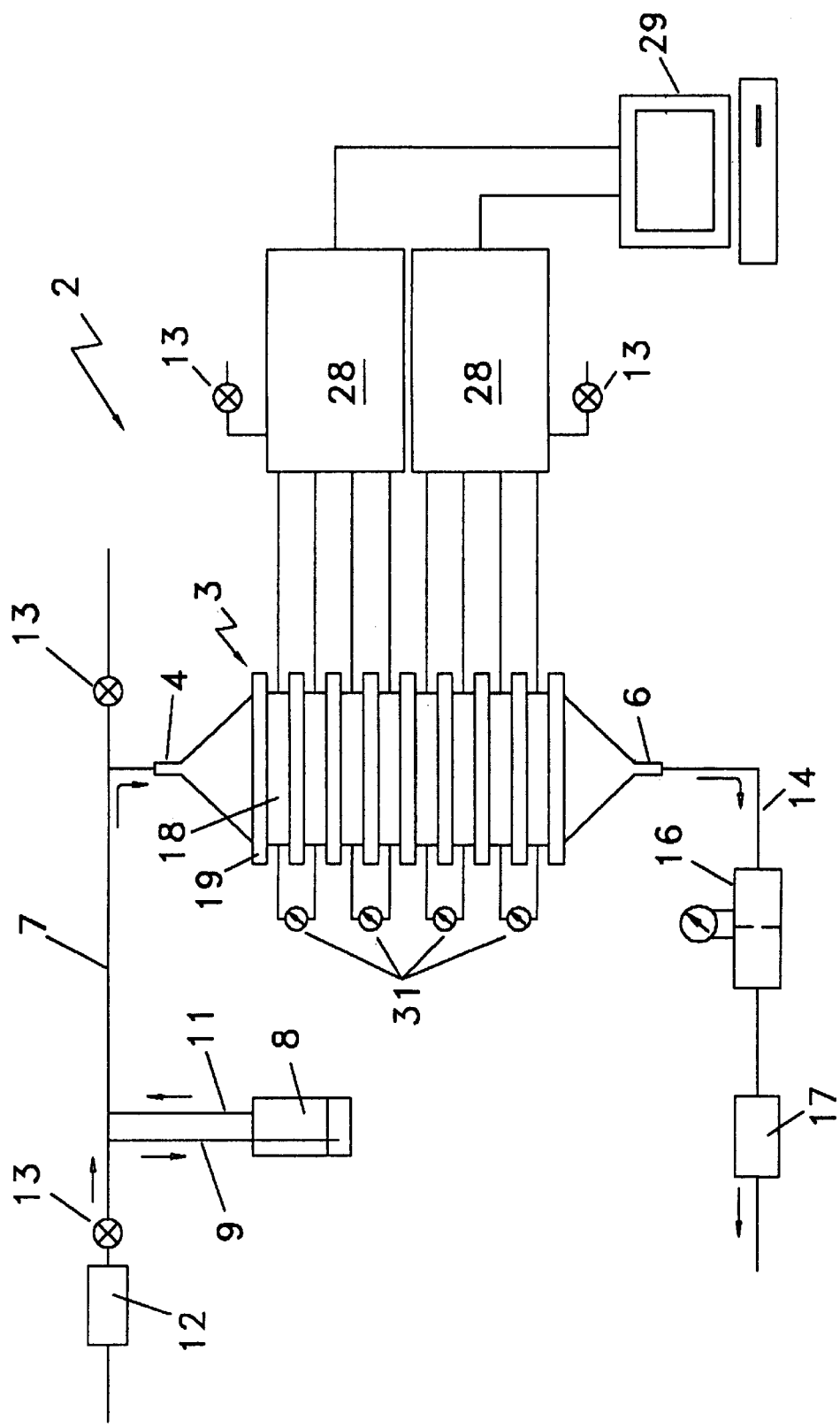
FIG. 1 is a schematic side plan view of the unique and novel structure utilized to carry out the inventive method of the present invention.

Referring to FIG. 1 of the drawings which discloses a side plan view of the unique structure to carry out the present invention, a comparative test stand arrangement 2 is disclosed for comparatively testing successive sample layers of fluid filter media of types presently known in the fluid filtration arts—as well as fluid filtration media yet to be developed. Although the present invention has particular applicability to the testing of numerous samples of air filter media, it is to be understood that the testing of other fluid filter media could also be successfully accomplished. Further, it is to be understood that the present invention has particular applicability to testing filter media samples of filter media arrangements such as employed in aforementioned Patent Application No. 08/996,222, filed on Dec. 22, 1997 by Kyung-Ju Choi, now U.S. Pat. No. 5,968,373.

As can be seen in FIG. 1 of the drawings, a longitudinally extending flow-through tower housing 3 is schematically disclosed as including an air test stream inlet 4 at the upstream end thereof and a downstream outlet 6 at the downstream end thereof. Although FIG. 1 discloses flow-through tower housing 3 with the flow axis disposed in a vertical position, it is to be understood that the flow-through housing flow axis can be positioned at other preselected angles, depending upon the nature of the selected commercial position of the filter media which are represented by the media samples to be tested.

Positioned upstream main compressed fluid line 7, which is connected to tower housing inlet 4, is a parallel connected particle generator or nebulizer 8. Inlet line 9 connected to main compressed fluid line 7 at one end thereof has the opposite end connected to the particle generator or nebulizer 8. An outlet line 11, parallel to and downstream of fluid line 9, connects the particle generator 8 at one end thereof to main compressed fluid line 7 at the other end thereof. Upstream the parallel connected particle generator 8 and in series with main compressed fluid line 7 is a high efficiency fluid filter (HEPA) 12. Suitable control valves 13 are provided upstream and downstream main compressed fluid line 7 and with particle counters described hereinafter. Downstream flow-through tower housing 3 is a main fluid outlet line 14 having a flow meter gauge 16 and an exhaust fluid outlet filter 17 connect in series with main fluid outlet line 14.

Referring to FIGS. 2–5 of the drawings and in accordance with one novel feature of the present invention, unique structure can be seen for assembling the flow-through tower housing 3 disclosed in schematic FIG. 1. This structure includes aligned flow-through spacer conduits in the form of modular incremental spacer rings 18 joined together by hinged clamps 19 (FIG. 2–4). Components as disclosed herein are commercially available as ISO-KF vacuum components, sold by MKS Instruments, Inc., Boulder, Colo. (see the above noted bulletin pages). It is to be understood that the present invention is not limited to the particular components disclosed herein and that the axial thicknesses thereof, as well as other types of commercially available components and latches could be utilized to assemble the tower housing 3. For example, spring loaded, adjustable, aligned ring components with over-center latches and screw-down mechanism could also be utilized, the components being of variable thicknesses as spacing demands might so indicate. In the embodiment disclosed, each ring 18 (FIG. 2) is provided with peripheral end lips 21, so that adjacent lips 21 of adjacent, aligned rings 18 can be engaged and surrounded by groove 22 extending along the inner periphery of hinged, split ring clamp 19 (FIGS. 3 and 4). A screw and thumb-bolt assembly 23 (FIG. 3), is utilized with split ring clamp 19 to hold the end lips 21 of adjacent aligned rings 18 together in fast relation. Before clamping the rings 18 firmly together, a fluid filter media testing sample 24 to be tested in flow-through tower housing is inserted between the lips 21 of adjacent rings 18. As can be seen in FIG. 2, testing sample 24 includes an appropriately sized fluid filter media test sample 26 to be tested which is tightly sealed along the periphery thereof to a flexible, compressible ring border ring 27, such as rubber, which is tightly clamped between adjacent peripheral end lips 21 of adjacent rings 18. The clamping of rings 18 is accomplished by split clamping ring 19 and the screw and thumb-bolt assembly 23. In schematic FIG. 1, eight (8) such rings 18 and nine (9) clamping rings 19 are disclosed in the flow-through tower housing assembly 3. However, it is to be understood that the number of rings and clamps to be utilized can be varied in accordance with the number of fluid filter media testing samples to be tested and the preselected spacing between test samples.

As can be seen in FIG. 1 of the drawings, each ring 18 is connected by suitable connecting lines to one of two particle counters 28, which in turn are connected by suitable connecting lines to a computer 29. Particle counters 28 can be of the laser type, using laser diodes, such as Model 5230 made by HIAC/ROYCO, or other suitable particle counters commercially available. Further, each of two adjacent and joined spacer rings 18 are connected to one of four differential pressure gauges 31, each of which gauges serves to measure the pressure drop across a testing sample 24 which might be associated with spacer rings 18.

The multi-layer fluid filter media test stand above described is particularly adapted for an airstream and can accommodate particle sizes up to thirty (30) micrometers in diameter and air velocities up to one thousand (1000) feet per minute (ft/min.). Optimum particle sizes can range from approximately zero point three (0.3) to ten (10) micrometers and optimum air velocities can range from approximately five (5) to six hundred (600) feet per minute (ft/min.). The particle generator or nebulizer 8 can be a collision nebulizer made by BGI, located at Waltham, Mass. As an example, potassium chloride (KCI) or sodium chloride (NaCl) particles can be utilized. The data acquisition can be done by personal computer 29 and the pressure drop across each of the filter media test samples is measured by differential pressure gauges 31, with air flow being measured by the orifice flow meter 16. One of the key features of the test stand is its ability to handle multi-stationed test samples at preselected spacing between samples.

Figure 6:
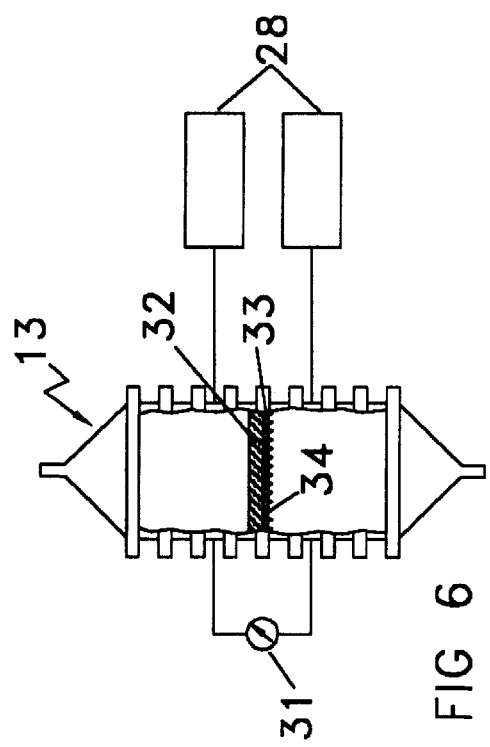
FIG. 6 is a partially broken away view of the schematic structure of FIG. 1, disclosing two aligned testing fluid filter media samples and back-up screen to be tested in assembled face-to-face relation in the novel testing tower of FIG. 1.

Various sample testing arrangements are disclosed in FIGS. 6 through 13. In FIG. 6, two aligned flat fluid filter media samples 32, 33 and rimmed cup sample support 34, respectively, are disclosed. Referring to FIG. 5, it is to be noted that cup sample support 34 includes an open, flow-through, low resistant, filter media support surface 35 and a compressible peripheral gasket 40 sized to firmly surround the rim and engage with the inner peripheries of one or more spacer rings 18. It is to be understood that instead of adjustable cup sample support 34, media sample peripheries can be sized and treated to be clamped between adjacent ring surfaces 18 in fixed position (FIGS. 2 and 4). This arrangement of filter 32, 33 and cup support 34 is disposed in a face-to-face package relation in the novel testing tower housing 13 with the leads of differential pressure gauge 31 and particle counters 28 being positioned on the upstream and downstream side of the package to determine pressure drop, fiber sizing, and spacing requirements of the arrangement.

Figure 7:
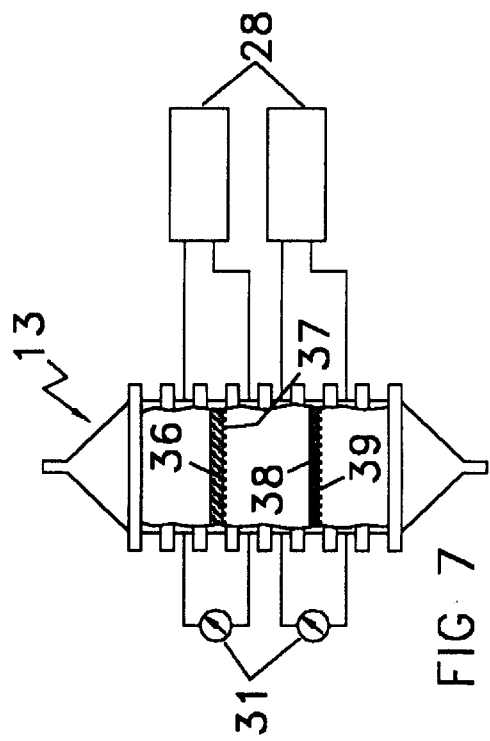
FIG. 7 discloses a similar testing arrangement as FIG. 7 with the two filter media samples in preselected spaced relation in the testing tower, each having a facing, downstream back-up screen.

In FIG. 7, a similar flat filter media sample 36 and a facing downstream screen 37 is shown as an upstream first package in test housing 13 and preselectively spaced therefrom in test housing 13 is flat filter media sample 38 and another facing downstream filter media support 39 as a second package. The leads of two differential pressure gauges 31 and two particle counters 28 are respectively positioned on the upstream and downstream face of each first and second package to determine appropriate pressure drop, fiber sizing and spacing of the arrangement.

Figure 8:
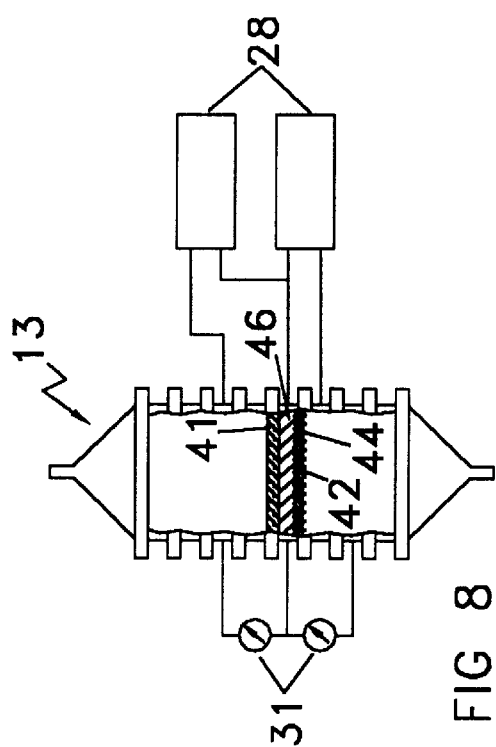
FIG. 8 discloses a similar testing arrangement as FIG. 6, here the two filter media samples to be tested being spaced from each other with an intermediate screen-like spacer therebetween facing the upstream face of the downstream testing sample and a back-up screen facing the downstream face of such downstream testing sample.
Figure 9:
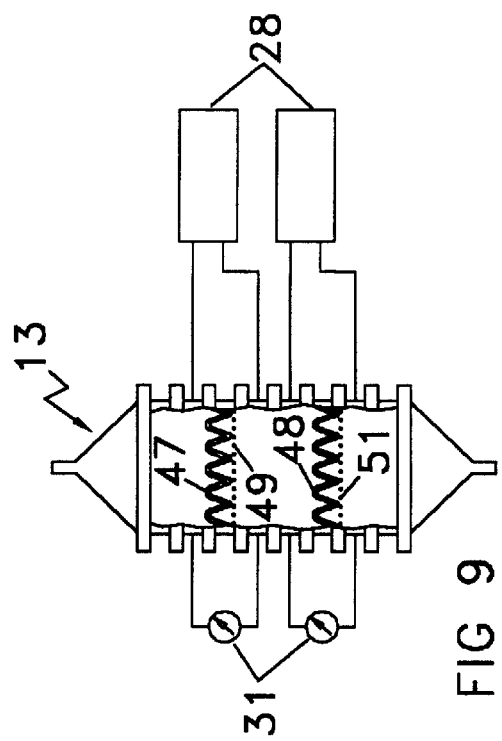
FIG. 9 discloses a similar testing arrangement as FIG. 7, here spaced, pleated filter media samples being shown, each with facing back-up screens.
Figure 10:
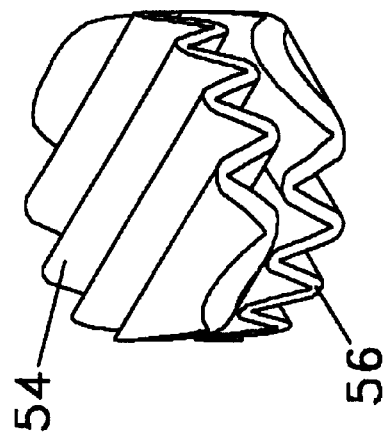
FIG. 10 discloses a schematic cross-sectional view of two pleated filter media samples which can be arranged to be tested in the testing tower of FIG. 1 with the crests in abutting relation.
Figure 11:
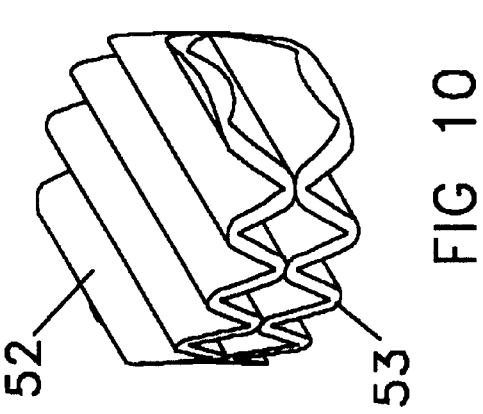
FIG. 11 is similar to the arrangement of FIG. 10, except that the crests of the two filter media samples to be tested are in crossing relation.

In FIG. 8, two preselectively spaced flat filter media test samples 41 and 42, with downstream sample 42 supported by facing downstream flat filter media support 44, the samples being shown in aligned, spaced position in tower housing 13 with a spacer 46 such as plastic netting or open scrim material therebetween and with the lines of differential pressure gauges 31 and particle counters 28 being selectively positioned upstream and downstream of selected parts of the assembly. FIG. 9 is similar to FIG. 7, only pleated sample test media supported by filter media supports 49 and 51 are shown as respectively spaced first and second packages disposed in tower test housing 13 with the leads for particle counters 28 and differential pressure gauges 31 being connected to the upstream and downstream faces of each first and second packages. Still another two filter media supports testing arrangements can be seen in FIGS. 10 and 11. In FIG. 10, testing media pleated samples 52 and 53 can be arranged for support and testing in housing 13 in crest abutting relationship or, as shown in FIG. 11, pleated samples 54 and 56 can be arranged in crest crossing relationship when supportedly disposed in test housing 13.

Figure 12:
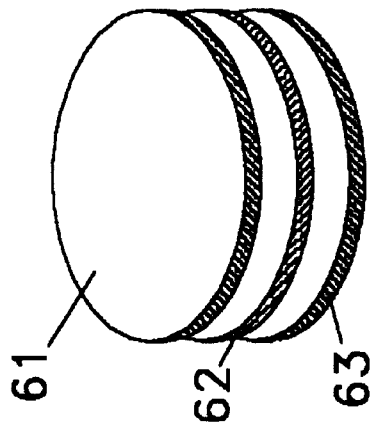
FIG. 12 is also similar to the arrangement of FIG. 10, except that one filter media sample to be tested is pleated and the other sample to be spaced from the pleated sample is flat; and, FIG. 13 is similar to the arrangement of FIG. 7 but here three filter media test samples are disclosed in preselected spaced relation.

In FIG. 12, an arrangement is disclosed wherein pleated filter media test sample 58 is positioned in aligned spaced relation from flat filter media test sample 59 as shown.

Figure 13:
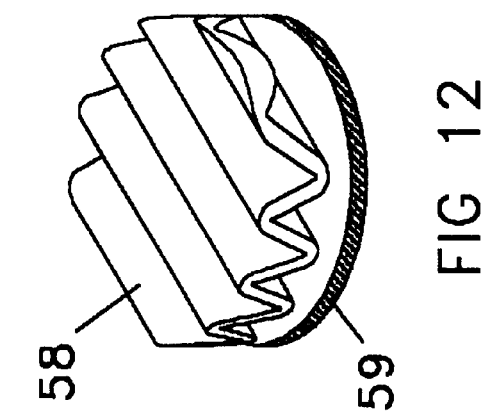

In FIG. 13, three spaced flat filter media test samples 61, 62, and 63 are shown in a spaced relative arrangement for testing in tower housing 13.

Thus, it can readily be seen from FIGS. 7–13 that the novel test stand structure allows for numerous testing combinations, all in accordance with the novel disclosure as set forth in the aforementioned U.S. Pat. No. 5,968,373, issued on Oct. 19, 1999, to Kyung-Ju Choi. In this prior patent, several different novel and inventive arrangements of filter media are described and the present application presents an inventive comparative testing method of filter media samples compatible with the teachings of the prior application and in which the several steps of such novel method can be accomplished with the above-described unique and novel apparatus, allowing a determination of appropriate fiber sizing, media contour, spacing and pressure drop control.

In carrying out the novel method of the present invention, at least two sample layers of filter media which correspond to those to be utilized for filtering purposes are successively positioned in a fluid confined flow-through test zone in a decreasing average pore size arrangement, the test zone including an upstream inlet and downstream outlet with the sample layers of filter media disposed in the confined zone between upstream inlet and downstream outlet so as to be in preselected relation to each other and to extend transversely across the line of fluid flow-though the confined zone with the edges of the filter media sample layers in sealed relation with the confined zone. In one advantageous embodiment of the invention, a measured particle laden fluid, having first been passed through a high efficiency filtering zone, is then introduced into the upstream inlet of the confined zone, the particle count which can be accomplished optically is measured upstream and downstream each sample layer, as is the differential pressure between the upstream and downstream side of each sample layer.

In another advantageous embodiment of the invention and in the novel testing method aforedescribed, the measured particles can be introduced into the test zone by compressed fluid, such as air, passing through a suitable particle generating zone with the fluid being metered in a flow metering zone downstream the confined flow-through test zone so as to meter the cubic feet per minute of fluid flow through the confined flow-through test zone. It is to be understood that testing can be accomplished in the flow-through test zone in any one of the several test sample arrangements as disclosed in FIGS. 7–14 or in other possible arrangements as the commercial situation to be met might dictate. It further is to be understood that fluid particle flow can also be accomplished (not shown) by utilizing an appropriate vacuum adjacent the downstream outlet of tower 13 or by a combination of compression and vacuum.

Although eight (8) testing stations are disclosed in the embodiment of FIG. 1, a higher or lower number of testing stations can be employed, as the commercial situation might dictate and within the physical limits of the testing equipment.

The invention claimed is:

1. A method of comparative testing at least two successive sample layers of filter media, each of preselectively differing and successively decreasing average pore size to be successively arranged in upstream-downstream respective alignment in a flow-through channel for removing particulate matter from a fluid stream to be treated in said channel comprising: assembling said preselected sample layers so that each can be separably supported by separate peripheral house forming spacer enclosures which can be assembled with other enclosures to form a confined flow-through test zone; successively positioning said supported sample layers of filter media which sample layers correspond to those to be utilized for filtering purposes with controlled average pore and fiber size arrangement respectively in said confined flow-through test zone including an upstream inlet and a downstream outlet; said corresponding sample layers of filter media being so supportedly disposed in said confined flow-through test zone between said upstream and said downstream outlet in preselected relation to each other to extend transversely across the line of fluid flow through said confined test zone with the edges of said filter media sample layers being in sealed relation with said confined flow-through test zone; introducing a measured particle laden fluid into said upstream inlet of said confined flow-through test zone; and, measuring the particle count in the fluid upstream and downstream side for each sample filter media layer.

2. The testing method of claim 1, wherein the measured particle count is accomplished by laser.

3. The testing method of claim 1, wherein said fluid introduced into said test zone is first passed through a high efficiency filtering zone.

4. The testing method of claim 3, wherein said measured particles in said fluid are introduced by compressed air passing through a particle generating zone.

5. The testing method of claim 3, wherein said fluid is passed through a flow metering zone downstream said confined flow-through test zone to meter and control the cubic feet per minute of fluid flow through said confined flow-through test zone.

6. The testing method of claim 1, wherein said successively positioned layers of sample filter media are in pleat crested form with adjacent crests abutting.

7. The testing method of claim 1, wherein said successively positioned layers of sample filter media are in pleat crested form with adjacent crests in spaced alignment.

8. The testing method of claim 1, wherein said successively positioned layers of sample filter media are in pleated form with adjacent crests crossing at a preselected angle.

9. The testing method of claim 1, wherein said successively positioned layers of sample filter media include at least one layer in pleated form and one layer in substantially flat form with the crests of the pleated layer abutting a face of the flat layer.

10. The testing method of claim 1, wherein each medium layer is designed so that the differential pressure across each medium layer is maintained substantially equal during testing period.

11. The testing method of claim 1, wherein said successive sample layers are preselectively spaced.

12. The testing method of claim 1, wherein the average flow pore size of the sample test layers decreases from upstream to downstream layers.

13. A method of comparative testing three successive sample layers of filter media, each of said three sample layers being of preselectively differing and successively decreasing average pore size with selected fiber sizes to be successively arranged in preselectively positioned upstream-downstream alignment in a flow-through channel for removing particulate matter from an air stream to be treated in said channel comprising: assembling each of said filter media layers so that each is separately supported by separate peripheral house forming spacer ring enclosures which can be assembled with other similar house forming spacer ring enclosures to form a confined housing test zone; positioning and sealingly supporting like corresponding supported sample layers of filter media in like corresponding decreasing average pore size arrangement with selected fiber sizes in said confined fluid flow-through test zone including an upstream inlet and a downstream outlet, said ring supported sample layers of filter media being disposed in said zone between said upstream inlet and said downstream outlet in like corresponding positioned, parallel relation to each other to extend transversely across the line of air stream flow through said confined test zone with the edges of said layers being in sealed relation with said confined test zone; passing a measured air stream destined for passing through said confined flow-through test zone first through a high efficiency filtering zone; introducing measured particles by compressed gases from a particle generating zone into said air stream to be measured; passing said measured particle laden air stream to said upstream inlet of said confined flow-through test zone; and measuring the particle count in said air stream upstream and downstream of each of the three positioned supported layers of filter media disposed in transversely sealed relation in said confined flow-through test zone.

14. A comparative test stand apparatus for comparatively testing successive sample layers of filter media to be utilized to optimize filtering capacity comprising: separate peripheral house forming spacer enclosures for each of said sample layers of filter media assembled in stacked relation to form a confined flow-through housing, said flow-through housing having a fluid test stream inlet to receive preselectively measured particle laden fluids to be tested and a fluid test stream outlet downstream said inlet with sample filter media spacer enclosures cooperatively mounted with respect to said flow-through housing between said inlet and outlet to successively receive and relatively position at least two layers of said sample filter media to be comparatively tested so that said layers are aligned with the fluid streams to be tested with the edges thereof in sealed relation with the inner wall faces of said flow-through housing; and; particle counter means associated with said housing to count particles in said fluid upstream and downstream in each sample filter media layer disposed in said housing.

15. The test stand apparatus of claim 14, said filter media spacer enclosures including an open, flow-through, low resistant filter media support surface forming a flow-through rimmed cup and a peripheral compressible gasket surrounding said cup to sealingly engage with said inner peripheral surface of said housing.

16. The test stand apparatus of claim 14, said particle counter means being of laser type.

17. The test stand apparatus of claim 14, said flow-through housing inlet having an upstream fluid conduit connected thereto which includes an upstream high efficiency fluid filter and a particle generator inlet conduit therebetween.

18. The test stand apparatus of claim 14, said filter media receptacle being relatively adjustable to preselectively vary the positioning between successive sample layers of filter media.

19. The test stand apparatus of claim 14, said apparatus including at least two flow-through peripheral spacer rings each with outer and inner peripheral surfaces, with said inner peripheral surface forming said inner peripheral surface of said housing, said spacer rings being of preselected thickness aligned and clamped together with said sample filter media receptacle peripheries aligned and sealingly clamped therebetween.

20. The test stand apparatus of claim 19, said apparatus including more than two flow-through spacer rings of preselected thickness to hold said filter media receptacles in preselected aligned and spaced relation.

21. The test stand apparatus of claim 19, said flow-through spacer rings being in the form of preselected rings clamped together.

22. The test stand apparatus of claim 21, said flow-through spacer rings each having outwardly extending peripheral lips extending from said outer surface to be tightly clamped together by a peripheral hinged clamp member.

23. A comparative test stand apparatus for comparatively testing successive sample layers of filter media to be utilized to optimize filtering capacity comprising: a longitudinally extending flow-through housing including a longitudinally extending inner peripheral surface having an air test stream inlet at one end thereof to receive preselectively measured particulate laden air streams to be tested in said housing and an air test stream outlet at the opposite end thereof to discharge said air stream from said housing; adjustable sample filter media aligned peripheral receptacle spacer rings including outer and inner peripheral surfaces with said outer surfaces assembled to form said flow-through housing having outwardly extending mating peripheral lips; hinged peripheral clamping means engageable with said lips, said spacer rings being cooperatively mounted with respect to said housing between said inlet and said outlet to successively receive and relatively position in preselective supported spaced relation said layers of filter media to be tested therebetween so that said selectively positioned supported layers are aligned with the air stream to be tested with said tips thereof in sealed relation; filter media support receptacles including open, flow-through, low resistant filter media support surfaces for forming flow-through rimmed support cups having inner and outer peripheral surfaces with said outer peripheral surfaces sized to be disposed within and sealingly and adjustably engage with said inner peripheries of said rings and said inner surfaces supporting said filter layers; laser particulate counter means associated with said housing to count particulates in said air stream upstream and downstream each sample filter media layer disposed between adjacent rings; said test stand air stream inlet in said housing having an upstream air stream conduit connected thereto which includes an upstream high efficiency air filter and a particulate inlet conduit therebetween, said particulate inlet conduit successively including a compressed air source, and, a particulate generator.

* * * * *